United States Patent [19]

Irvine

[11] 4,020,179
[45] Apr. 26, 1977

[54] 7-SUBSTITUTED-2-INDOLINONES

[75] Inventor: John L. Irvine, West Allis, Wis.

[73] Assignee: Richardson-Merrell Inc., Wilton, Conn.

[22] Filed: May 15, 1975

[21] Appl. No.: 577,631

[52] U.S. Cl. .............................. 424/274; 260/325 R
[51] Int. Cl.² ................ A61K 31/40; C07D 209/38
[58] Field of Search .................. 260/325 R; 424/274

[56] References Cited

UNITED STATES PATENTS

| 3,686,210 | 8/1972 | Bell et al. | 260/325 R |
|---|---|---|---|
| 3,801,593 | 4/1974 | Bell et al. | 260/325 R |

OTHER PUBLICATIONS

Mills et al., "J. Chem. Soc." vol. 1961, pp. 5558–5559 (1961).

Primary Examiner—Dolph H. Torrence
Attorney, Agent, or Firm—L. Ruth Hattan; Eugene O. Retter; George W. Rauchfuss, Jr.

[57] ABSTRACT

The compounds are 7-substituted-2-indolinones which are useful as anticonvulsant agents. Representative of the compounds are 7-chloro-3-hydroxy-3-phenyl-indolin-2-one, 7-bromo-3-hydroxy-3-phenyl-2-indolinone, and 7-chloro-3-hydroxy-3-methyl-2-indolinone.

10 Claims, No Drawings

7-SUBSTITUTED-2-INDOLINONES

BACKGROUND OF THE INVENTION

Structurally related compounds are disclosed in U.S. Pat. Nos. 3,686,210; 3,801,593, 3,441,570; and 3,773,759, as well as the following references: J. Het. Chem., 6, 599 (1969); J. Med. Chem., 15, 762 (1972); Khim.Farm. Zh. 6, 11–13 (1972), CA, 78: 43182p; and Khim. Farm. Zh. 28, 23 (1968), CA 69: 106404Z.

DETAILED DESCRIPTION

The novel compounds of the present invention have the following formula:

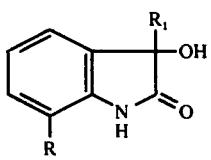

in which R is a halogen such as chloro, bromo or fluoro and trifluoromethyl, and $R_1$ is a lower alkyl of 1 to 4 carbon atoms such as methyl, ethyl or isopropyl, an aralkyl of 7 to 13 carbon atoms such as benzyl, phenethyl or chlorobenzyl, or an aryl such as phenyl, or a nuclear-substituted phenyl such as methoxyphenyl or chlorophenyl.

The compounds of the present invention may be conveniently prepared employing as the starting material an isatin of the formula:

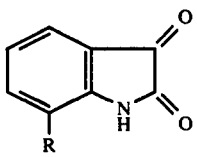

in which R is as previously described. The isatins used as starting materials are known compounds which are easily prepared by standard procedures or are commercially available.

Representative of the isatins that may be employed are the following:
7-chloroisatin,
7-bromoisatin,
7-fluoroisatin, and
7-trifluoromethylisatin.

In the preferred method the compounds are prepared by reacting the 7-substituted isatin with organometallic reagents such as phenyl lithium or a Grignard reagent. The reactants are preferably combined in an anhydrous solvent such as ethyl ether or tetrahydrofuran. The reaction is preferably conducted at reflux temperatures. When the reaction is substantially complete, a saturated ammonium chloride solution is added to hydrolyze the Grignard adduct to the desired tertiary alcohol. The resulting product can then be isolated from the reaction mixture by conventional means such as evaporation of the solvent. The described process may be illustrated as follows:

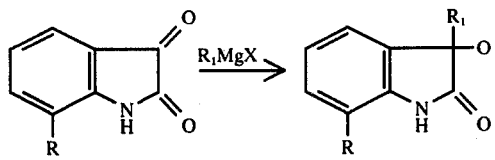

in which R and $R_1$ are as previously described and X is a reactive halogen.

Representative of the Grignard reagents which may be employed are the following:
phenylmagnesium bromide,
phenylmagnesium iodide,
4-chlorobenzylmagnesium bromide,
3,4-dichlorobenzylmagnesium bromide,
benzylmagnesium bromide,
4-methoxybenzylmagnesium bromide,
4-chlorophenylmagnesium bromide,
3,4-dichlorophenylmagnesium bromide,
4-methoxyphenylmagnesium bromide,
4-fluorophenylmagnesium bromide,
4-trifluoromethylphenylmagnesium bromide,
3-trifluoromethylphenylmagnesium bromide, and
3-chlorobenzylmagnesium bromide.

The above-described Grignard reagents may be prepared by conventional methods such as those described in U.S. Pat. No. 2,996,503 and German Patent No. 1,109,166.

Representative of the compounds which may be prepared by the described process are the following:
7-chloro-3-hydroxy-3-phenyl-2-indolinone,
7-fluoro-3-hydroxy-3-phenyl-2-indolinone,
7-bromo-3-hydroxy-3-phenyl-2-indolinone,
7-chloro-3-hydroxy-3-methyl-2-indolinone,
7-fluoro-3-hydroxy-3-methyl-2-indolinone,
7-trifluoromethyl-3-hydroxy-3-methyl-2-indolinone,
7-chloro-3-hydroxy-3-p-chlorophenyl-2-indolinone,
7-chloro-3-hydroxy-3-p-methoxyphenyl-2-indolinone,
7-chloro-3-hydroxy-3-(3,4-dichlorophenyl)-2-indolinone, and
7-chloro-3-hydroxy-3-benzyl-2-indolinone.

The novel compounds of the invention have been shown to possess anticonvulsant activity in animals. For example, the compound 7-chloro-3-hydroxy-3-phenyl-2-indolinone has been shown in standard animal tests to produce significant anticonvulsant activity as demonstrated by antimetrazol and anti-electroshock activity, which is indicative of medullary depressant action. The compound was administered in these tests in doses of 80–100 mg/kg prior to challenge.

In behavioral screening tests the compounds of the present invention exhibit a central nervous system depressant activity. In mice receiving 100–1000 mg/kg of the compounds intraperitoneally in the form of a 5% acacia suspension, reactivity, posture, righting reflex and muscle tone were depressed. As a result of the behavioral tests, the compounds were found to have an oral $LD_{50}$ in excess of 300 mg/kg. The behavioral studies were conducted in accordance with the procedure set forth by Irwin in "Animal and Clinical Pharmacologic Techniques in Drug Evaluation", J. H. Nodine and P. E. Siegler, Ed., Year Book Publishers, Inc., 1964, pp. 36–54.

When they are intended for pharmaceutical use, it is preferred to combine the compounds with pharmaceutical additives such as diluents, flavoring agents, disintegrating agents, and the like, and form them into unit dosage forms. Especially preferred are tablets, capsules, suspensions for oral administration and sterile solutions for parenteral administration. Such dosage forms will normally contain about 50 to 250 mg. of the active ingredient.

A typical tablet can have the following composition:

|  | Mg. |
|---|---|
| 7-chloro-3-hydroxy-3-phenyl-indolin-2-one | 50 |
| Lactose U.S.P. | 136.5 |
| Corn starch | 20 |
| Corn starch (as 10% starch paste) | 3.4 |
| Magnesium stearate | 1.3 |

The tablets are formed using a 5/16 inch diameter punch for compression.

Capsules may be prepared by filling No. 3 hard gelatin capsules with the following ingredients:

|  | Mg. |
|---|---|
| 7-chloro-3-hydroxy-3-phenyl-indolin-2-one | 50 |
| Lactose U.S.P. | 200 |
| Starch U.S.P. | 16 |
| Talc U.S.P. | 8 |

In clinical practice the daily dosage of the active ingredient may range from about 50 mg. to 500 mg. The exact amount, of course, will be conditioned upon the severity of the patient's condition and other factors taken in account in good medical practice.

The following examples illustrate the practice of the invention:

EXAMPLE 1

7-Chloro-3-hydroxy-3-phenyl-2-indolinone

A Grignard reagent prepared from 62 g. magnesium, 400 g. bromobenzene in two liters tetrahydrofuran (THF) is added to 181 g. (1.0 mole) 7-chloroisatin (1a) in two liters THF at a rate to keep a gentle reflux. After three hours of reflux, the reaction is cooled and decomposed with 350 ml. saturated ammonium chloride, filtered, and the THF stripped to give a dark oil. The oil is dissolved in aqueous sodium hydroxide and precipitated with hydrochloric acid. Recrystallization from aqueous ethanol gives 7-chloro-3-hydroxy-3-phenyl-2-indolinone, m.p. 154°–156°.

Anal. Calcd. for $C_{14}H_{10}ClNO_2$: C, 64.75; H, 3.88; N, 5.40; Cl, 13.66. Found: C, 64.64; H, 3.96; N, 5.32; Cl, 13.55.

EXAMPLE 2

7-Bromo-3-hydroxy-3-phenyl-2-indolinone

This product is prepared in an analogous manner to that described in Example 1. The 7-bromo-3-hydroxy-2-indolinone obtained has a melting point of 153°–156°.

Anal. Calcd. for $C_{14}H_{10}BrNO_2$: C, 55.31; H, 3.30; N, 4.61; Br, 26.29. Found: C, 55.12; H, 3.31; N, 4.63; Br, 26.20.

EXAMPLE 3

3-Hydroxy-7-methyl-3-phenyl-2-indolinone

This product is prepared in an analogous manner to that described in Example 1. The 3-hydroxy-7-methyl-3-phenyl-2-indolinone obtained has a melting point of 173°–175°.

Anal. Calcd. for $C_{15}H_{13}NO_2$: C, 75.38; H, 5.48; N, 5.86. Found: C, 75.11; H, 5.48; N, 5.94.

EXAMPLE 4

7-Chloro-3-hydroxy-3-methyl-2-indolinone

This product is prepared in an analogous manner to that described in Example 1, using methyl iodide for bromobenzene and anhydrous ethyl ether in place of tetrahydrofuran solvent. The 7-chloro-3-hydroxy-3-methyl-2-indolinone obtained has a melting point of 195°–199°.

Anal. Calcd. for $C_9H_8ClNO_2$: C, 54.70H, 4.08; N, 7.09; Cl, 17.94. Found: C, 54.69; H, 4.11; N, 7.15; Cl, 17.96.

EXAMPLE 5

7-Chloro-3-hydroxy-1-methyl-3-phenyl-2-indolinone

The product is prepared as in Example 1 using 7-chloro-1-methylisatin in place of 7-chloroisatin and omitting the sodium hydroxide treatment. Crystallization with acetonitrile gives a solid byproduct, 7-chloro-3,3-diphenyl-1-methyl-2-indolinone. The oil from the mother liquor gives a yellow solid on crystallization from benzene/heptane. Chromatography over silica gel with ethyl acetate eluent and recrystallization from nitromethane gives 7-chloro-3-hydroxy-1-methyl-3-phenyl-2-indolinone, m.p. 125°–127°.

Anal. Calcd. for $C_{15}H_{12}ClNO_2$: C, 65.75; H, 4.41; N, 5.11, Cl, 12.94. Found: C, 65.65; H, 4.47; N, 5.13; Cl, 12.87.

I claim:

1. A compound of the formula

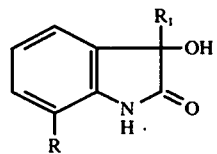

I in which R is chloro, bromo, fluoro or trifluoromethyl, and $R_1$ is lower alkyl of 1 to 4 carbon atoms, phenyl, benzyl, phenethyl, chlorobenzyl, chlorophenyl, methoxyphenyl or dichlorophenyl, or pharmaceutically acceptable salts thereof.

2. A compound of claim 1 in which R is chloro.
3. A compound of claim 1 in which R is bromo.
4. The compound of claim 1 which is 7-chloro-3-hydroxy-3-phenyl-2-indolinone.
5. The compound of claim 1 which is 7-bromo-3-hydroxy-3-phenyl-2-indolinone.
6. The compound of claim 1 which is 7-chloro-3-hydroxy-3-methyl-2-indolinone.
7. The compound of claim 1 in which $R_1$ is chlorophenyl.
8. The compound of claim 1 in which $R_1$ is methoxyphenyl.
9. A pharmaceutical composition comprising a compound of claim 1 in combination with a pharmaceutical diluent.
10. The method of controlling convulsions in animals which comprises administering to an animal susceptible to such convulsions a safe and effective anticonvulsant amount of a compound of claim 1.

* * * * *

UNITED STATES PATENT AND TRADEMARK OFFICE
CERTIFICATE OF CORRECTION

PATENT NO. : 4,020,179
DATED : April 26, 1977
INVENTOR(S) : John L. Irvine

It is certified that error appears in the above-identified patent and that said Letters Patent are hereby corrected as shown below:

Column 2, formula between lines 1 and 9 should appear as follows:

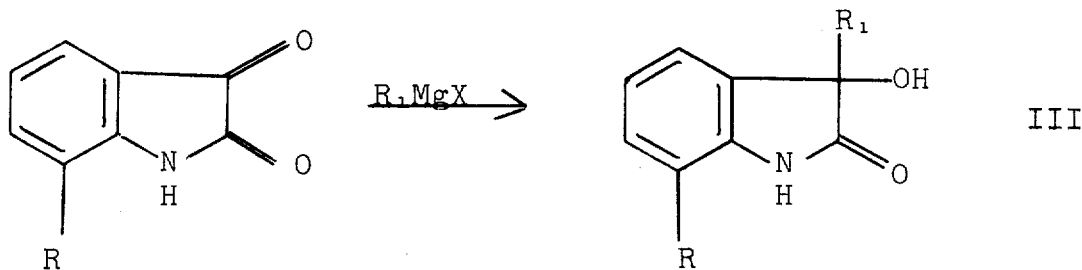

Column 3, lines 64 and 65 should read as follows:

"7-bromo-3-hydroxy-3-phenyl-2-indolinone"

$\mathfrak{Signed}$ and $\mathfrak{Sealed}$ this fifth Day of July 1977

[SEAL]

Attest:

RUTH C. MASON
*Attesting Officer*

C. MARSHALL DANN
*Commissioner of Patents and Trademarks*